United States Patent [19]

Diana et al.

[11] 4,232,161
[45] Nov. 4, 1980

[54] 4-[6-(2-CHLORO-4-METHOXYPHENOXY)-HEXYL]-3,5-DIETHYL-1-(2-PYRIDINYL)-1H-PYRAZOLE

[75] Inventors: Guy D. Diana, Stephentown; Philip M. Carabateas, Schodack, both of N.Y.

[73] Assignee: Sterling Drug Inc., New York, N.Y.

[21] Appl. No.: 87,880

[22] Filed: Oct. 24, 1979

Related U.S. Application Data

[62] Division of Ser. No. 8,412, Feb. 1, 1979, which is a division of Ser. No. 822,246, Aug. 5, 1977, Pat. No. 4,171,365.

[51] Int. Cl.³ .................................. C07D 401/04
[52] U.S. Cl. .................................. 546/279; 424/263
[58] Field of Search .................................. 546/279

[56] References Cited

U.S. PATENT DOCUMENTS 4,031,246   6/1977   Collins et al. .................. 424/331

FOREIGN PATENT DOCUMENTS 281957   7/1952   Switzerland .

OTHER PUBLICATIONS

Grandberg et al., J. Gen. Chem. of the USSR, 1960, vol. 30, pp. 2916–2919.

*Primary Examiner*—Alan L. Rotman
*Assistant Examiner*—Natalia Harkaway
*Attorney, Agent, or Firm*—Thomas L. Johnson; B. Woodrow Wyatt

[57] ABSTRACT

4-(Aryloxyalkyl)pyrazoles of the formula

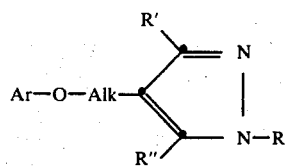

useful as antiviral agents, are prepared by reacting the corresponding diketones of the formula Ar-O-Alk-CH(COR')COR" with hydrazine or a substituted hydrazine H₂NNHR. Mono- or bis-pyrazoles are similarly obtained from bis-diketones of the formula

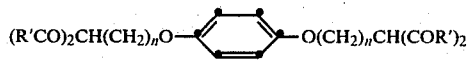

1 Claim, No Drawings

4-[6-(2-CHLORO-4-METHOXYPHENOXY)HEXYL]-3,5-DIETHYL-1-(2-PYRIDINYL)-1H-PYRAZOLE

This application is a division of application Ser. No. 008,412, filed Feb. 1, 1979, which is in turn a division of Ser. No. 822,246, filed Aug. 5, 1977, now U.S. Pat. No. 4,171,365.

BACKGROUND OF THE INVENTION (a) Field of the Invention

The invention relates to aryloxyalkylpyrazoles, to the preparation thereof and to compositions and methods for the use thereof as antiviral agents.

(b) Description of the Prior Art

Sterling Drug U.S. Pat. No. 4,031,246, issued June 21, 1977, discloses compounds useful as pesticidal and antiviral agents and having the formula

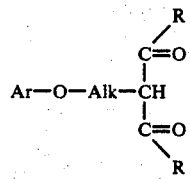

wherein Ar is phenyl or substituted phenyl, Alk is alkylene of 3–10 carbon atoms and R is lower-alkyl. These compounds are intermediates in the preparation of the compounds of the instant invention.

Grandberg et al., J. General Chem. of the USSR, 30, 2916–2919 (September - December 1960) discloses, inter alia, 4-benzyl-3,5-dimethylpyrazole. No biological properties are disclosed for the latter compound.

SUMMARY OF THE INVENTION

In a composition of matter aspect, the invention relates to 4-(aryloxyalkyl)pyrazoles and pharmaceutically acceptable acid-addition salts thereof, said pyrazoles having the formula

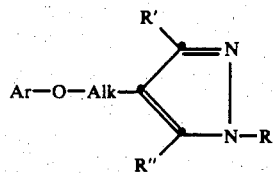

wherein Ar is phenyl or substituted phenyl, Alk is an alkylene bridge, and R, R' and R" are selected substituents as defined hereinbelow.

In a further composition of matter aspect, the invention relates to phenylenedioxy compounds of the formulas

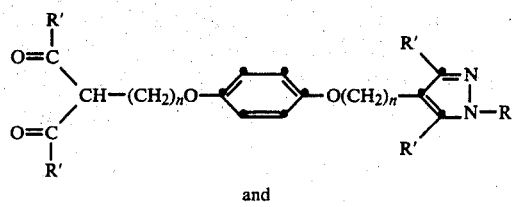

and

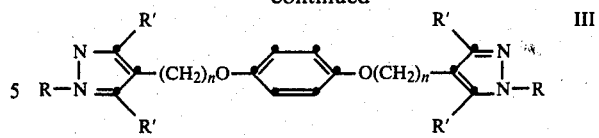

wherein R is hydrogen or lower-alkyl, R' is lower-alkyl and n is an integer from 3 to 7; and acid-addition salts of said compounds.

In a further composition of matter aspect, the invention relates to a composition for combatting viruses which comprises an antivirally effective amount of a compound of formula I, II or III in admixture with a suitable carrier or diluent.

In a process aspect, the invention relates to a process for preparing a compound of formula I which comprises reacting a diketone of the formula Ar—O—Alk—CH(COR')COR" with a hydrazine of the formula H₂NNHR.

In a further process aspect, the invention relates to a process for preparing a compound of formula II or III which comprises reacting a bis-diketone of the formula

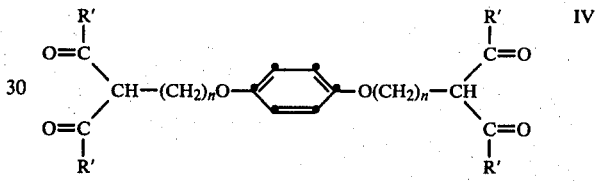

with a hydrazine of the formula H₂NNHR.

In a further process aspect, the invention relates to a method for combatting viruses which comprises contacting the locus of sid viruses with an antivirally effective amount of at least one compound of formula I, II or III.

DETAILED DESCRIPTION INCLUSIVE OR PREFERRED EMBODIMENTS

A preferred aspect of the invention relates to compounds of formula I above wherein R is hydrogen, alkyl of 1 to 6 carbon atoms, hydroxyalkyl of 1 to 6 carbon atoms, carboalkoxyalkyl of 3 to 6 carbon atoms, or phenyl; R' is alkyl of 1 to 4 carbon atoms or phenyl; R" is alkyl of 1 to 4 carbon atoms, phenyl or hydroxy; Alk is alkylene of 3 to 10 carbon atoms optionally interrupted by an oxygen atom separated by at least two carbon atoms from the terminal bonds of Alk; and Ar is phenyl or phenyl substituted by from 1 to 3 substituents selected from the group consisting of halo, hydroxy, nitro, alkyl of 1 to 4 carbon atoms, lower-alkoxy of 1 to 4 carbon atoms, alkylthio of 1 to 4 carbon atoms, hydroxyalkyl of 2 to 4 carbon atoms, benzyloxy and trifluoromethyl.

Compounds of formula I where the group R is tertiary-amino-lower-alkyl, tertiary-amino-lower-alkanoyl or pyridyl are also within the purview of the invention.

In the above general formula I, Alk stands for a saturated aliphatic hydrocarbon bridge containing from 3 to 10 carbon atoms. The alkylene bridge may be straight or branched. A preferred class of compounds are those where Alk is straight chain alkylene of 3 to 10 carbon atoms, and if the Alk bridge is branched, it is preferred that it be symmetrical, that is with the branching at the same relative positions from either end of the bridge.

The alkylene bridge, Alk, is optionally interrupted by an oxygen atom separated by at least two carbon atoms from the terminal bonds of Alk. The oxygen atom is preferably in the center of the alkylene bridge, equidistant from the terminal bonds of Alk.

The carbon chains of R and R' can be straight or branched, thus including methyl, ethyl, propyl, isopropyl, butyl, isobutyl, secondary-butyl and tertiary-butyl.

When two or three monovalent substituents are present on the phenyl ring of Ar, they can be the same or different. When halo substituents are present, they can be any of the four common halogens, fluoro, chloro, bromo or iodo.

The compounds of formula I are prepared by interacting a diketone or keto-ester of the formula

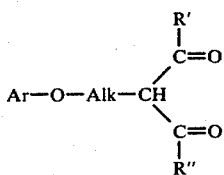

wherein R' is lower-alkyl and R" is lower-alkyl or lower-alkoxy, with hydrazine or a derivative thereof of the formula H₂NNHR. The intermediate diketones and keto-esters are obtained as described in copending application Ser. No. 576,311, filed May 12, 1975, now U.S. Pat. No. 4,031,246, issued June 21, 1977, the disclosure of which is incorporated herein by reference. The reaction is carried out by heating the reactants together, preferably at a temperature between about 50° and 100° C. in an inert solvent for a period ranging from several minutes to several hours. Stoichiometrically equivalent amounts of the reactants may be used, although a slight excess of hydrazine reactant is generally employed.

In the event a keto-ester (R" is lower-alkoxy) is used as the starting material, the alkoxy group is cleaved during the course of the reaction and a compound of formula I wherein R" is OH is obtained.

Alternatively, it is possible to prepare compounds of formula I where R is alkyl by alkylation of the corresponding compounds of formula I where R is hydrogen with an alkyl halide in the presence of a strong base, preferably in an inert solvent under anhydrous conditions.

A further aspect of the invention relates to compounds of formulas II or III, given above, wherein R is hydrogen or lower-alkyl of 1 to 6 carbon atoms; R' is alkyl of 1 to 4 carbon atoms; and n is an integer from 3 to 7.

The compounds of formulas II and III are prepared by interacting a compound of formula IV, given above, with hydrazine or a derivative thereof of the formula H₂NNHR. Substantially equimolar quantities of bis-diketone IV and hydrazine give a monopyrazole of formula II. The use of two or more molecular equivalents of hydrazine relative to the bis-diketone products a bispyrazole of formula III. The reaction conditions are essentially the same as those used to prepare compounds of formula I.

The intermediate bis-diketones (IV) are in turn prepared by one of two methods (a) or (b), as follows:

(a) Interacting hydroquinone with two molar equivalent amounts of a compound of the formula Hal-$(CH_2)_n CH(COR')_2$, where Hal is bromine or iodine, in the presence of a base in an inert organic solvent. The haloalkyldiketone reactant is in turn prepared by interacting a dihalide $Hal(CH_2)_n Hal$ with the alkali metal salt of a diketone, $R'COCH_2COR'$.

(b) Interacting a compound of the formula 4-[Hal-$(CH_2)_n$—O]—$C_6H_4$—O—$(CH_2)_n$-Hal, where Hal is bromine or iodine, with an alkali metal salt of a diketone, $R'COCH_2COR'$, in an inert solvent. The bishalide reactant is in turn prepared by interacting hydroquinone with an alkylene dihalide, $Hal(CH_2)_n Hal$.

In the event that acid-addition salts of the compounds of the invention are prepared and used, the nature of the anion is not critical provided it is relatively non-toxic to mammals and thus pharmaceutically acceptable. Such anions include chloride, bromide, iodide, sulfate, nitrate, phosphate, acetate and other alkanoates such as hexanoate and nonanoate; lactate, tartrate, cyclohexylsulfamate and various sulfonates such as methanesulfonate, tosylate and naphthalenesulfonate.

The structures of the compounds of the invention were established by the modes of synthesis, by elementary analysis, and by infrared and nuclear magnetic resonance spectral determinations.

Biological evaluation of the compounds of the invention has shown that they possess antiviral activity. They are thus useful in combatting viruses present on inanimate surfaces as well as viral infections in animal organisms. The in vitro testing of the compounds of the invention against herpes simplex viruses types 1 and 2 and rhinovirus 14 has showed that they inhibited viral growth at minimum concentrations (MIC) ranging from about 0.7 to about 50 micrograms per milliliter. The MIC values were determined by standard serial dilution procedures. In vivo activity has also been demonstrated in the treatment of mouse genital herpes simplex type 2 infection.

The antiviral compositions are formulated by preparing a dilute solution or suspension in an organic or aqueous-organic medium, for example ethyl alcohol, acetone, dimethylsulfoxide, and the like; and are applied to the locus to be disinfected by conventional means such as spraying, swabbing or immersing. Alternatively, the compounds can be formulated as ointments or creams by incorporating them in conventional ointment or cream bases, such as alkylpolyether alcohols, cetyl alcohol, stearyl alcohol and the like; as jellies by incorporating them in conventional jelly bases such as glycerin and tragacanth; or as aerosol sprays or foams. The antivirally effective component of the composition is present in a concentration of between about 0.7 parts per million and about 5 percent by weight, depending upon the chemical species used, the object to be treated and the type of formulation employed. For disinfection of inanimate surfaces with aqueous or aqueous-organic solutions, concentrations in the lower part of the range are effective. For topical application in medical or veterinary use in the form of ointment, cream, jelly or aerosol, concentrations in the upper part of the range are preferred.

The following examples will further illustrate the invention.

EXAMPLE 1

4-[6-(2-Chloro-4-methoxyphenoxy)hexyl]-3,5-diethyl-1H-pyrazole [I; Ar is 2-Cl-4-CH$_3$OC$_6$H$_3$, Alk is (CH$_2$)$_6$, R is H, R' and R" are C$_2$H$_5$].

Hydrazine hydrate (15.7 ml, 0.32 m) was added over a 20 min. period to a slurry of 100 g (0.272 m) of 4-[6-(2-chloro-4-methoxyphenoxy)hexyl]-3,5-heptanedione in 300 ml of methanol. The internal temperature rose to a maximum of 50° C. during the addition. The reaction mixture was heated at reflux for one hour, and the solvent was then removed in vacuo. The residue was dissolved in 300 ml of methylene dichloride and the resulting solution was washed with three 100 ml portions of water. The organic layer was dried over anhydrous sodium sulfate and the solvent was evaporated to leave 100 g of 4-[6-(2-chloro-4-methoxyphenoxy)hexyl]-3,5-diethyl-1H-pyrazole as a colorless oil.

The free base thus obtained was dissolved in 250 ml of ethyl acetate and the solution was treated with a solution of 19.3 ml (0.30 m) of methanesulfonic acid in 50 ml of ethyl acetate. The mixture was filtered and colored to 5° C. for two hours. The solid which had formed was collected by filtration and dried overnight in vacuo at 40° C. to yield 105.5 g (84.5%) of 4-[6-(2-chloro-4-methoxyphenoxy)hexyl]-3,5-diethyl-1H-pyrazole in the form of its methanesulfonate salt, m.p. 91°-93° C. An additional 14.0 g (11%), m.p. 90°-92° C. was obtained from the mother liquor by evaporation and recrystallization of the residue from ethyl acetate.

A mixture of 18.5 g (0.05 m) of 4-[6-(2-chloro-4-methoxyphenoxy)hexyl]-3,5-heptanedione and 5 ml of 100% hydrazine hydrate in 100 ml of absolute ethanol was heated at reflux for five hours. The reaction mixture was concentrated in vacuo, the residue dissolved in 50 ml of ethanol, and the solution made acid with hydrochloric acid. The latter solution was concentrated in vacuo and the residue crystallized twice from an isopropyl alcohol-ether mixture to give 14.5 g of 4-[6-(2-chloro-4-methoxyphenoxy)hexyl]-3,5-diethyl-1H-pyrazole in the form of its hydrochloride salt, m.p. 117°-118° C. The corresponding hydrobromide salt had the m.p. 118°-120° C.

A mixture of 18.25 g (0.05 m) of 4-[6-(2-chloro-4-methoxyphenoxy)hexyl]-3,5-diethyl-1H-pyrazole in the free base form and 7.9 g (0.05 m) of nonanoic acid was warmed on a steam bath. The reaction mixture was filtered through activated charcoal and degassed at 50° C. (0.1 mm) to give 12.7 g of the nonanoic acid acid-addition salt of 4-[6-(2-chloro-4-methoxyphenoxy)hexyl]-3,5-diethyl-1H-pyrazole as a pale yellow liquid.

Anal. Calcd. for C$_{20}$H$_{29}$ClN$_2$O$_2$.C$_9$H$_{18}$O$_2$: C, 66.58; H, 9.06; Cl, 6.78. Found: C, 66.67; H, 9.00; Cl, 6.89.

4-[6-(2-Chloro-4-methoxyphenoxy)hexyl]-3,5-diethyl-1H-pyrazole methanesulfonate when tested in vitro against herpes simplex type 1 (herpes 1), herpes simplex type 2 (herpes 2) and human rhinovirus type 14 showed antiviral activity at minimal inhibitory concentrations (MIC) of 3-6, 6 and 3 micrograms per milliliter, respectively. The compound was also effective in treatment of mice vaginally infected with herpes simplex type 2; survival rates of 80-100% were observed after intravaginal administration of a 10% aqueous solution of the compound in saturated cotton tampons.

By procedures similar to those used in Example 1, and starting with the appropriate aryloxyalkyl diketone, Ar—O—Alk—CH(COR') COR", and hydrazine or substituted hydrazine, H$_2$NNHR, the following compounds were prepared in yields varying from about 30 to 90 percent.

EXAMPLE 2

4-[6-(4-Methoxy-2-nitrophenoxy)hexyl]-3,5-diethyl-1H-pyrazole

[I; Ar is 4—CH$_3$O—2—O$_2$NC$_6$H$_3$, Alk is (CH$_2$)$_6$, R is H, R' and R" are C$_2$H$_5$], hydrochloride salt, m.p. 103°-105° C., yellow solid from acetonitrile; MIC=1 microg/ml (herpes 2).

EXAMPLE 3

4-[6-(2-Chloro-4-nitrophenoxy)hexyl]-3,5-diethyl-1H-pyrazole

[I; Ar is 2—Cl—4—O$_2$NC$_6$H$_3$, Alk is (CH$_2$)$_6$, R is H, R' and R" are C$_2$H$_5$], hydrochloride salt, m.p. 130°-132° C., colorless solid from acetonitrile.

EXAMPLE 4

4-[6-(4-Bromophenoxy)hexyl]-3,5-diethyl-1H-pyrazole

[I; Ar is 4—BrC$_6$H$_4$, Alk is (CH$_2$)$_6$, R is H, R' and R" are C$_2$H$_5$], free base, m.p. 78°-80° C., colorless solid from acetonitrile. The intermediate 4-[6-(4-bromophenoxy)hexyl]-3,5-heptanedione had the m.p. 31°-33° C.

EXAMPLE 5

4-[6-(2-Chloro-4-methoxyphenoxy)hexyl]-3,5-diethyl-1-methyl-1H-pyrazole

[I; Ar is 2—Cl—4—CH$_3$OC$_6$H$_3$, Alk is (CH$_2$)$_6$, R is CH$_3$, R' and R" are C$_2$H$_5$], free base, colorless liquid, b.p. 190°-195° C. (0.01 mm), purified by chromatography on silica with ether; MIC=6 microg/ml (herpes 2).

EXAMPLE 6

4-[5-(2-Chloro-4-methoxyphenoxy)pentyl]-3,5-diethyl-1-methyl-1H-pyrazole

[I; Ar is 2—Cl—4—CH$_3$OC$_6$H$_3$, Alk is (CH$_2$)$_5$, R is CH$_3$, R' and R" are C$_2$H$_5$], free base, yellow oil, b.p. 190°-200° C. (0.1 mm), purified by chromatography on silica; MIC=3 microg/ml (herpes 2).

EXAMPLE 7

4-[6-(2-Chloro-4-methoxyphenoxy)hexyl]-3,5-dimethyl-1H-pyrazole

[I; Ar is 2—Cl—4—CH$_3$OC$_6$H$_3$, Alk is (CH$_2$)$_6$, R is H, R' and R" are CH$_3$], hydrochloride salt, m.p. 150°-151° C., off-white crystals from acetonitrile; MIC=3 microg/ml (herpes 2).

EXAMPLE 8

4-[6-(2-Chloro-4-methoxyphenoxy)hexyl]-1,3,5-trimethyl-1H-pyrazole

[I; Ar is 2—Cl—4—CH$_3$OC$_6$H$_3$, Ar is (CH$_2$)$_6$, R, R' and R" are CH$_3$], free base, pale yellow oil, b.p. 200°-205° C. (0.03 mm), purified by chromatography on silica; MIC=0.7 microg/ml (herpes 2).

EXAMPLE 9

4-{2-[2-(2-Chloro-4-methoxyphenoxy)ethoxy]ethyl}-3,5-diethyl-1H-pyrazole

[I; Ar is 2—Cl—4—CH$_3$OC$_6$H$_3$, Alk is (CH$_2$)$_2$O(CH$_2$)$_2$, R is H, R' and R" are C$_2$H$_5$], hydrochloride salt, m.p.

90°-92° C., off-white needles from ethyl acetate; MIC=12 microg/ml (herpes 2).

EXAMPLE 10

4-[6-(2,5-Dichloro-4-methoxyphenoxy)hexyl]-3,5-diethyl-1H-pyrazole

[I; Ar is 2,5—$Cl_2$—4—$CH_3OC_6H_2$, Alk is $(CH_2)_6$, R is H, R' and R'' are $C_2H_5$], hydrochloride salt, m.p. 148°-150° C., colorless crystals from acetonitrile.

EXAMPLE 11

4-[6-(2-Chloro-4-hydroxyphenoxy)hexyl]-3,5-diethyl-1H-pyrazole

[I; Ar is 2—Cl—4—$HOC_6H_3$, Alk is $(CH_2)_6$, R is H, R' and R'' are $C_2H_5$], hydrochloride salt, m.p. 109°-111° C., colorless crystals from acetonitrile and 2-butanone; MIC=12 microg/ml (herpes 2). The starting material for this preparation was 4-[6-(2-chloro-4-benzoyloxyphenoxy)hexyl]-3,5-heptanedione (prepared from 2-chloro-4-benzoylphenol and 4-(6-bromohexyl)-3,5-heptanedione). The benzoyl group was hydrolyzed during the procedure.

EXAMPLE 12

4-[6-(2-Chloro-4-methoxyphenoxy)hexyl]-3,5-diethyl-1H-pyrazole-1-ethanol

[I; Ar is 2—Cl—4—$CH_3OC_6H_3$, Alk is $(CH_2)_6$, R is $CH_2CH_2OH$, R' and R'' are $C_2H_5$]. The product was distilled at 215°-225° C. (0.05 mm) and chromatographed on silica with ethyl acetate to yield the free base as a pale yellow oil; MIC=12 microg/ml (herpes 2).

Anal. Calcd. for $C_{22}H_{33}ClN_2O_3$: C, 64.61; H, 8.13; Cl, 8.64. Found: C, 64.77; H, 8.10; Cl, 9.01.

EXAMPLE 13

Ethyl 4-[6-(2-chloro-4-methoxyphenoxy)hexyl]-3,5-diethyl-1H-pyrazoleacetate

[I; Ar is 2—Cl—4—$CH_3OC_6H_3$, Alk is $(CH_2)_6$, R is $CH_2COOC_2H_5$, R' and R'' are $C_2H_5$].

A mixture of 18.45 g of 4-[6-(2-chloro-4-methoxyphenoxy)hexyl]-3,5-heptanedione, 7.73 g of carbethoxymethylhydrazine hydrochloride and 5 g of triethylamine in 100 ml of absolute ethanol was heated at reflux for 8 hours. The product was isolated and distilled to give 16.7 g of ethyl 4-[6-(2-chloro-4-methoxyphenoxy)hexyl]-3,5-diethyl-1H-pyrazoleacetate as a pale yellow oil, b.p. 205°-210° C. (0.05 mm); MIC=6-12 microg/ml (herpes 1 and 2).

EXAMPLE 14

4-[5-(2-Chloro-4-methoxyphenoxy)pentyl]-3,5-diethyl-1H-pyrazole

[I; Ar is 2—Cl—4—$CH_3OC_6H_3$, Alk is $(CH_2)_5$, R is H, R' and R'' are $C_2H_5$], hydrochloride salt, m.p. 80°-83° C., colorless solid from isopropyl acetate; MIC=6-12 microg/ml (herpes 2).

EXAMPLE 15

4-[4-(2-Chloro-4-methoxyphenoxy)butyl]-3,5-diethyl-1H-pyrazole

[I; Ar is 2—Cl—4—$CH_3OC_6H_3$, Alk is $(CH_2)_4$, R is H, R' and R'' are $C_2H_5$], hydrochloride salt, beige needles from isopropyl acetate; MIC=6-12 microg/ml (herpes 2).

EXAMPLE 16

4-[7-(2-Chloro-4-methoxyphenoxy)heptyl]-3,5-diethyl-1H-pyrazole

[I; Ar is 2—Cl—4—$CH_3OC_6H_3$, Alk is $(CH_2)_7$, R is H, R' and R'' are $C_2H_5$], hydrochloride salt, colorless powder from isopropyl acetate; MIC=6 microg/ml (herpes 2).

EXAMPLE 17

4-[7-(2-Chloro-4-methoxyphenoxy)heptyl]-1,3,5-trimethyl-1H-pyrazole

[I; Ar is 2—Cl—4—$CH_3OC_6H_3$, Alk is $(CH_2)_7$, R, R' and R'' are $CH_3$], chromatographed on silica with ether, and distilled to give the free base as a pale yellow oil, b.p. 175°-185° C. (0.1 mm); MIC=0.7-1.5 microg/ml (herpes 2), 1.5 (herpes 1).

EXAMPLE 18

4-[6-(2-Chloro-4-methoxyphenoxy)hexyl]-3,5-diethyl-1-phenyl-1H-pyrazole

[I; Ar is 2—Cl—4—$CH_3OC_6H_3$, Alk is $(CH_2)_6$, R is $C_6H_5$, R' and R'' are $C_2H_5$], chromatographed on silica with chloroform:ether 97:3, and distilled to give the free base as a yellow oil, b.p. 215°-220° C. (0.05 mm); MIC=3 microg/ml (herpes 2).

EXAMPLE 19

4-(6-Phenoxyhexyl)-3,5-diethyl-1H-pyrazole

[I; Ar is $C_6H_5$, Alk is $(CH_2)_6$, R is H, R' and R'' are $C_2H_5$], hydrochloride salt, m.p. 119°-121° C., colorless solid from isopropyl acetate.

EXAMPLE 20

4-[6-(4-Chlorophenoxy)hexyl]-3,5-diethyl-1H-pyrazole

[I; Ar is 4—$ClC_6H_4$, Alk is $(CH_2)_6$, R is H, R' and R'' are $C_2H_5$], hydrochloride salt, m.p. 130°-132° C., colorless solid from acetonitrile; MIC=3 microg/ml (herpes 2).

EXAMPLE 21

4-[6-(2-Chloro-4-methoxyphenoxy)hexyl]-5-methyl-1H-pyrazol-3-ol

[I; Ar is 2—Cl—4—$CH_3OC_6H_3$, Alk is $(CH_2)_6$, R is H, R' is $CH_3$, R'' is OH].

A mixture of 11.1 g (0.03 m) of ethyl 2-acetyl-8-(2-chloro-4-methoxyphenoxy)octanoate, 2.73 g (0.03 m) of thiosemicarbazide and 1.62 g (0.03 m) of sodium methoxide in 15 ml of methanol was heated at reflux for 24 hours. The solid product was collected, washed with 50% aqueous ethanol and recrystallized from ethanol to give 5.6 g of 4-[6-(2-chloro-4-methoxyphenoxy)hexyl]-5-methyl-1H-pyrazol-3-ol, m.p. 145°-146° C.; MIC=6 microg/ml (herpes 2). (During this reaction the thiocarbamyl group ($CSNH_2$) of the thiosemicarbazide was cleaved so that the reaction product is the same as that obtained when unsubstituted hydrazine is used.)

EXAMPLE 22

4-[6-(2-Chloro-4-methoxyphenoxy)hexyl]-1-(2-dimethylaminoethyl)-3,5-diethyl-1H-pyrazole

[I; Ar is 2—Cl—4—$CH_3OC_6H_3$, Alk is $(CH_2)_6$, R is $CH_2CH_2N(CH_3)_2$, R' and R'' are $C_2H_5$], free base, yellow oil, b.p. 210°–215° C. (0.03 mm); MIC=6 microg/ml (herpes 2).

EXAMPLE 23

4-[6-(4-Methoxyphenoxy)hexyl]-3,5-diethyl-1H-pyrazole

[I; Ar is 4—$CH_3OC_6H_4$, Alk is $(CH_2)_6$, R is H, R' and R" are $C_2H_5$], hydrochloride salt, m.p. 103°–105° C., colorless solid from acetonitrile.

EXAMPLE 24

4-[6-(2-Chloro-4-methoxyphenoxy)hexyl]-3,5-diethyl-1-(2-pyridinyl)-1H-pyrazole

[I; Ar is 2—Cl—4—$CH_3OC_6H_3$, Alk is $(CH_2)_6$, R is 2-pyridinyl, R' and R" are $C_2H_5$], free base, pale yellow oil, b.p. 215°–222° C. (0.025 mm); MIC=6 microg/ml (herpes 2).

We claim:
1. 4-[6-(2-Chloro-4-methoxyphenoxy)hexyl]-3,5-diethyl-1-(2-pyridinyl)-1H-pyrazole.

* * * * *

UNITED STATES PATENT AND TRADEMARK OFFICE
CERTIFICATE OF CORRECTION

PATENT NO. : 4,232,161
DATED : November 4, 1980
INVENTOR(S) : Guy D. Diana and Philip M. Carabateas It is certified that error appears in the above-identified patent and that said Letters Patent are hereby corrected as shown below:

Column 2, in formula III,

" 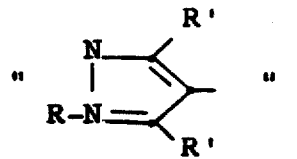 " should read -- 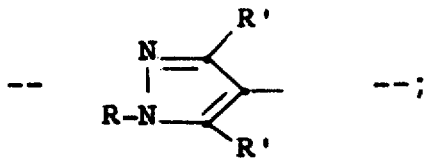 --;

line 38, "sid" should read --said--; line 42, "OR" should read --OF--.

Column 3, line 60, "products" should read --produces--.

Column 5, line 22, "colored" should read --cooled--.

Signed and Sealed this

Twenty-fourth Day of March 1981

[SEAL]

Attest:

RENE D. TEGTMEYER

Attesting Officer   Acting Commissioner of Patents and Trademarks